United States Patent [19]

Frost

[11] Patent Number: 5,475,935
[45] Date of Patent: Dec. 19, 1995

[54] JUMPING ASSIST SYSTEM

[76] Inventor: John H. Frost, 23520 Califa St., Woodland Hills, Calif. 91367

[21] Appl. No.: 280,226

[22] Filed: Jul. 25, 1994

Related U.S. Application Data

[63] Continuation-in-part of Ser. No. 80,823, Jun. 24, 1993, abandoned.

[51] Int. Cl.⁶ .............................. A43B 7/32; A61H 1/00
[52] U.S. Cl. ................... 36/89; 36/114; 602/27
[58] Field of Search .................. 36/88, 89, 92, 36/114; 602/27, 23, 28, 29

[56] References Cited

U.S. PATENT DOCUMENTS

| | | | |
|---|---|---|---|
| 1,708,156 | 4/1929 | Scroggins | 36/89 |
| 4,237,874 | 12/1980 | Nelson | 602/27 |
| 4,289,122 | 9/1981 | Mason et al. | 602/27 |
| 4,454,871 | 6/1984 | Mann et al. | 602/27 |
| 4,523,394 | 6/1985 | Lindh et al. | 36/89 |
| 4,924,605 | 5/1990 | Spademan | 36/114 |
| 4,941,273 | 7/1990 | Gross | 36/114 |
| 4,977,891 | 12/1990 | Grim | 602/27 |
| 5,022,390 | 6/1991 | Whiteside | 602/23 |
| 5,056,509 | 10/1991 | Swearington | 36/89 |
| 5,088,479 | 2/1992 | Detoro | 602/27 |
| 5,090,138 | 2/1992 | Borden | 36/89 |
| 5,125,171 | 6/1992 | Stewart | 36/89 |
| 5,125,400 | 6/1992 | Johnson, Jr. | 602/27 |
| 5,144,943 | 9/1992 | Luttrell et al. | 602/27 |
| 5,291,671 | 3/1994 | Caberlotto et al. | 36/89 |

FOREIGN PATENT DOCUMENTS

| | | | |
|---|---|---|---|
| 964740 | 8/1950 | France | 36/89 |
| 309978 | 12/1918 | Germany | 36/89 |

Primary Examiner—Steven N. Meyers
Attorney, Agent, or Firm—Jack C. Munro

[57] ABSTRACT

A jumping assist system to be mounted in conjunction with each lower leg and foot of a human which will cause the imparting of additional energy during the jumping movement which will result in the individual being able to jump higher, especially in a succession of jumps, as well as having greater endurance in jumping. When the lower leg moves forwardly into the jump-ready position, a pulling force is applied from the lower leg to a tension brace which extends substantially parallel to the back of the leg to under the heel of the foot causing a forward rotational force at the ankle joint. This force will assist the individual in the jumping action. There is also a separate strap connection over the dorsum of the foot which extends along the bottom of the foot and under the heel, anchoring in the achilles area. This dorsum strap further assists in achieving an increased level of upward support and some rotational force that assists the individual in the jumping motion.

28 Claims, 6 Drawing Sheets

JUMPING ASSIST SYSTEM

REFERENCE TO PRIOR APPLICATION

This application is a continuation-in-part of patent application Ser. No. 08/080,823, filed Jun. 24, 1993, now abandoned, entitled JUMPING ASSIST SYSTEM, by the same inventor.

BACKGROUND OF THE INVENTION

1) Field of the Invention

The field of this invention relates to devices to assist a human in jumping and further to a system utilized in conjunction with each lower leg and foot of the human which will result in greater energy being obtained in the jumping motion.

2) Description of Prior Art

In the sport of basketball, players not only jump to significant heights, but they are continually jumping as well as running over long periods of time. Regardless of their athletic ability, players will lose endurance in jumping as the basketball game is played.

Basketball shoes in the past have been designed to assist players in the jumping action. However, this assistance has been limited to the designing of the soles to be shock absorbing or to have a certain amount of elasticity so as to somewhat assist the jumper in the jumping action. However, this assistance has been relatively minimal. There has not been known, prior to the present invention to the present inventor, any device which takes into account certain movements of the leg and foot during the jumping action and connects to the human's leg and foot a device which increases the jumping force by harnessing the energy of those certain movements.

Within the prior art there have been attempts at designing springing devices in conjunction with shoes. One example of such a device is shown within U.S. Pat. No. 5,090,138, issued Feb. 25, 1992 to Robert Borden. In this patent to Borden there is shown a spring strap vertically connecting a shin brace and a heel socket. The shin brace and heel socket are connected by an ankle hinge axis. Borden's structure is highly dysfunctional for several reasons. In order for a force to move an object, the force must be independent of the object. One can't lift a box if one is standing on the box. Borden's shin brace 14 cannot lift heel socket 12 via spring strap 38 because the shin brace 14 is attached to the heel socket 12 at ankle hinge 16. The heel socket 12 and shin brace 14 are pulling on each other. A problem encountered by the current inventor is to maintain the shin brace in place. Bordon's shin brace 14 is held in place by the ankle hinge 16 so the ankle hinge 16 will likewise hold the heel socket 12 in place preventing any upward thrust.

Any rotational movement at ankle hinge 16 would also be unlikely because the human ankle joint not only rotates but moves forwardly as much as an inch when moving into the jump-ready position. That is, when the foot contacts the ground, the whole lower leg moves forwardly including the ankle joint and achilles area, which is depicted incorrectly in FIG. 2 of Borden as though the leg were broken at the ankle or made of rubber. Borden has created a binding isosceles triangle with spring strap 38 as the base and ankle hinge point 16 the top. When the jumper's knee bends and the lower leg moves forwardly into the jump-ready position, the jumper's ankle joint at the ankle hinge 16 area also moves forwardly. Yet for a lengthening to occur at spring strap 38, ankle hinge 16 and spring strap 38 must move closer together as the triangle flattens. The reverse would occur when the jumper's foot moves into an obtuse angle at lift-off. The net result is the structure of Borden will bind up.

In the present invention, the jumper's foot is free to move independently of the force applied to it, and there is no binding problem. In the preferred embodiment, the force which propels the foot to lift-off position is supported by an angle brace which is in turn supported by the ground under the shoe, with no attachment or support to the angle brace from the upper leg. The converting of force from the forward motion of the human leg to upward motion of the heel occurs over a much larger distance than the stretching distance of Borden's spring strap, so there is far greater energy return. A leg strap is anchored at the shin area. As the jumper's leg bends at the knee causing the shin to move forward and further away from the heel, a tremendous force is exerted between the shin and the heel through a connecting brace/strap by way of the achilles area which lengthens horizontally the full extent of the forward motion of the lower leg, and extends vertically to connect to the heel itself, pulling up on the heel to increase jumping power.

The standard ankle wrap long used by athletes in all sports is a triangular pattern extending horizontally across (or around) the ankle, then extending down from both sides and both ends of the ankle to under the heel/arch area then back up to connect at both the back and front of the ankle. It is completely interconnected to bind up the ankle and prevent injury. A different method of wrapping was tried by the present inventor. This method did not bind the ankle but rather created a pulling force upward on the heel. The wrap looked U-shaped, not triangular, as it extended from the shin to the achilles to the heel to the dorsum, with no direct connection between the shin and the dorsum or shin and heel. Jumping was easier and higher. However, after some use, the wrap would gradually pull down the leg losing its tension and most of its value, no matter how well the wrap had been taped.

The solution to the shin anchoring problem came with the conception of an inverted, steel angle brace (a shelf support brace) anchored to the sole of the shoe, then extending up to the top of the achilles area where a pivot point (such as a pulley) is located to guide a cable from the shin horizontally to the achilles area (so the force does not pull down at the shin), and then vertically to a soft sling directly under the heel itself, which is separate from the angle brace or shoe.

It is this (1) horizontal pulling and (2) separation of heel sling from the shoe, with an independent entity (the ground) which supports the shoe which supports the pulling force at the pulley on the angle brace that eliminates the problem of two or more forces working against each other and the two chief elements which make the current invention different from all those preceding. If Borden could eliminate the ankle hinge which creates the triangular binding similar to the conventional ankle wrap, the Borden invention might work except there would then be nothing to hold up the shin brace (it would pull down). Even if Borden's spring strap connected directly to the heel rather than to the heel socket, the triangular binding pattern would still be present due to the ankle hinge. Also, the pulling force would be minimal since it does not derive from the large, forward movement of the leg, but only from a slight movement of the achilles area. The only embodiment of Borden which eliminates the triangular binding pattern is the coil spring pivot axis, but the previously mentioned forward motion of the rotating ankle joint going into the jump-ready position would still cause a binding problem, plus the jumping force is far too great for a spring of that size to control.

Detoro, U.S. Pat. No. 5,088,479, teaches a device which resembles the subject invention in appearance only. It serves a completely different purpose. In the present invention, the angle brace is claimed only in conjunction with the supporting of flexible braces or straps which are completely different from any straps of Detoro, which merely serve as attachments. In the present invention, the dorsum tension brace or strap 1) mimics the tendons underlying the arch which support the foot against collapse when weight is placed on the ball of the foot at the jump-ready position, thus allowing greater ease in heel movement upwards in relation to the ball, and 2) receives energy from the force of expansion of the dorsal foot due to the weight of the jumper. The brace or strap is flexible but not elastic and extends between its attachment to the foot in the dorsum area and its attachment separate from the foot in the achilles area. The energy return helps overcome gravity going into the jump. Also, in the present invention, the dorsum tension brace does not fix the device to the foot. It attaches only to the rigid angle brace in the upper achilles area. In Detoro, there are shown three dorsum straps which attach the sleeve 28 to the patient's foot at three velcro fastener areas 30. There is no direct connection (or pulling force) between the front of the foot and the achilles area (either lower or upper). Therefore, there is no force pulling the foot into the desired obtuse angle, lift-off position.

The device of Mann et al., U.S. Pat. No. 4,954,871, is referred to as ribs 18 and 20 on each side of the foot within a mold, which is in an entirely different location than that of the present invention. The resulting orthosis of Mann et al. securely maintains the foot and leg in a slightly less than ninety degree angle, rigidity enhanced by the ribs. In the present invention, the foot has its normal full range of movement. In Mann et al. there is no attachment to the ribs by any straps similar to the dorsum tension brace of the present invention.

A further attempt at designing a device which would propel a user to greater jumping heights is what is shown within U.S. Pat. No. 4,941,273, issued Jul. 17, 1990, to Theodore S. Gross. In Gross, because there is no rigid support of the Gross strap, equivalent to the angle brace of the present invention, heelstrike would actually shorten the distance between anchor points because of the cushiony heel which would lessen the tension. It appears that lift-off would cause tension due to bending of the foot at the ball area, but then it is too late as tension must occur going into the jump. Moreover, the "artificial tendon" of Gross will not work as a tendon because its forward anchoring point is in the shoe.

SUMMARY OF THE INVENTION

When jumping occurs, the human first must move into the jump-ready position. The at-rest position of the leg and the foot is with the foot being located at a substantially right angle to the longitudinal axis of the lower leg. When the individual moves into the jump-ready position, the lower leg of the individual moves forward which causes an acute angle to be produced between the longitudinal center axis of the lower leg and the longitudinal axis of the foot. Harnessing power from the forward leg movement can be done by connecting the shin area to the heel via the achilles area causing upward pull on the heel. At this time the individual's downward weight movement also causes a slight spreading and lengthening of the foot which is unnoticeable except by close examination. This invention seeks to both limit this movement and harness energy provided by this movement. The individual then pushes off the ball of the foot at which time the foot will leave the ground or floor creating an obtuse angle between the lower leg and the foot in the lift-off position. The jumping assist system of the present invention is basically dormant during the time that the foot is in the at-rest position and during the time that the obtuse angle is created between the leg and the foot at lift-off. However, when the individual moves into the jump-ready position, a pulling force is applied to a tension brace which is located along the back of the lower leg to beneath the heel of the foot, with this tension brace being located parallel to the achilles tendon. The upper end of the tension brace is connected by a strap to the front part or shin of the lower leg. The lower end of the brace is essentially fixed in position relative to the heel of the foot. When the lower leg extends forwardly, the distance between the shin and heel increases such that a stretching occurs along the length of the brace producing a pulling force so that at the time the jumping is initiated this pulling force causes the foot to snap with greater force from the jump-ready position to the lift-off position. The tension can be mostly an elastic system located separate from the shoe or it can be a cable system guided by a semi-rigid angle brace of spring steel type strength fixed to the sole of the shoe.

An objective of the present invention is to construct a jumping assist system of two versions. A simple one-piece "soft" version worn directly on the foot under the shoe, and a multiple-part mechanical version built into the shoe, both which will assist the human in jumping, the latter to a greater degree. This objective is to be accomplished primarily by harnessing the force created by the weight of the human's body moving the leg forward at the shin and applying that force directly under the heel for increased upward lift and secondarily by controlling and harnessing energy from the flattening, lengthening and widening movement of the foot which occurs going into the jump when the foot contacts the floor momentarily under the individual's force of weight during forward and sideways motion.

DETAILED DESCRIPTION OF THE SHOWN EMBODIMENT

Referring particularly to the drawings, there is shown the first embodiment 20 of the jumping assist system of this invention. The jumping assist system 20 is shown mounted in conjunction with a human foot 22 which has a dorsum 24 which is in the metatarsal area of the foot 22. Foot 22 also includes a bottom surface which forwardly has a ball 26 and rearwardly a heel 28. Located upwardly of the heel 28 is an ankle joint 30. Located above the ankle joint 30 is the lower leg 32. The back edge of the lower leg 32, which extends to the heel 28 is defined as the achilles area 34. The front edge of the lower leg 32 is defined as the shin 35.

Located directly adjacent and in alignment with the achilles area 34 is a tension brace 36. This tension brace 36 includes a heel sling 38 which encompasses the heel 28. Fixedly secured to the upper end of the tension brace 36 is a lower leg strap 40. This strap 40 is to have overlapping ends which secure together by interlocking hook and eye pads forming a releasable fastener 42. The use of such releasable fasteners is deemed to be conventional and is conventionally marketed under the trade name of VELCRO. The use of such a fastener 42 is for the purpose of accommodating different sizes of lower legs 32 to thereby make the jumping assist system 20 usable in conjunction with different individuals.

It is to be noted that the heel sling 38 surrounds the heel 28 and has an enlarged opening 44 through which the heel 28 extends. The material of construction for the heel sling 38 could be leather, fabric or rubber. The remaining portion of the brace 36 includes a strip that could be constructed of fabric or leather but likely would be a strong rubber material. This strip is shown to be an inch to two inches wide and is basically located to be parallel to the achilles tendon (not shown).

When the user proceeds to the jump-ready position, the lower leg 32 will move forwardly into the jump-ready position, with the anchoring point of the tension brace 36 at the lower leg strap 40 moving forwardly thus increasing the distance between the anchoring point at the lower leg strap 40 and the heel sling 38 thus exerting a force backward and downward on the lower leg strap 40, and upward on the heel sling 38 such that the opposing force on the lower leg strap 40 from the forward weight and motion of the body will help overcome resistance at the heel 28 due to gravity, thus pulling the heel 28 upward and increasing the propulsion of the jump.

To further assist in the application of the pulling force, there may be utilized a dorsum tension brace 46. The dorsum tension brace 46 is also to have ends which are to be secured together by a releasable fastener 48 which is basically similar to fastener 42. The dorsum tension brace 46 will be constructed of a fabric, leather or similar type of material similar to the lower leg strap 40. The dorsum tension brace 46 is fixedly secured underneath the ball 26 to a forward extension 50 which is located along the bottom of the foot 22 in between the ball 26 and the heel 28. The forward extension 50 will normally be constructed of a more rigid material and may be comprised of plastic, metal or may also include some type of a strong fabric. It is important to note that unlike a conventional ankle wrap which limits movement in all directions, there is no connection of straps between the shin 35 and dorsum 24.

When using the dorsum tension brace 46, the amount of the pulling force in a jumping procedure is magnified in two ways. One, within the achilles tension brace 36, the dorsum tension brace 46 functions to keep the heel sling 38 in its proper place and prevents the heel sling 38 from moving rearwardly. Rearward movement of the heel sling 38 will diminish the amount of pulling force that is created within the achilles tension brace 36. Two, depending on usage of materials and how such are connected, some force from the shin 35 to the heel 28 may extend further to the dorsum 24 causing a downward force on the dorsum 24 contributing to the desired rotational movement at the ankle joint 30.

Figure 1:
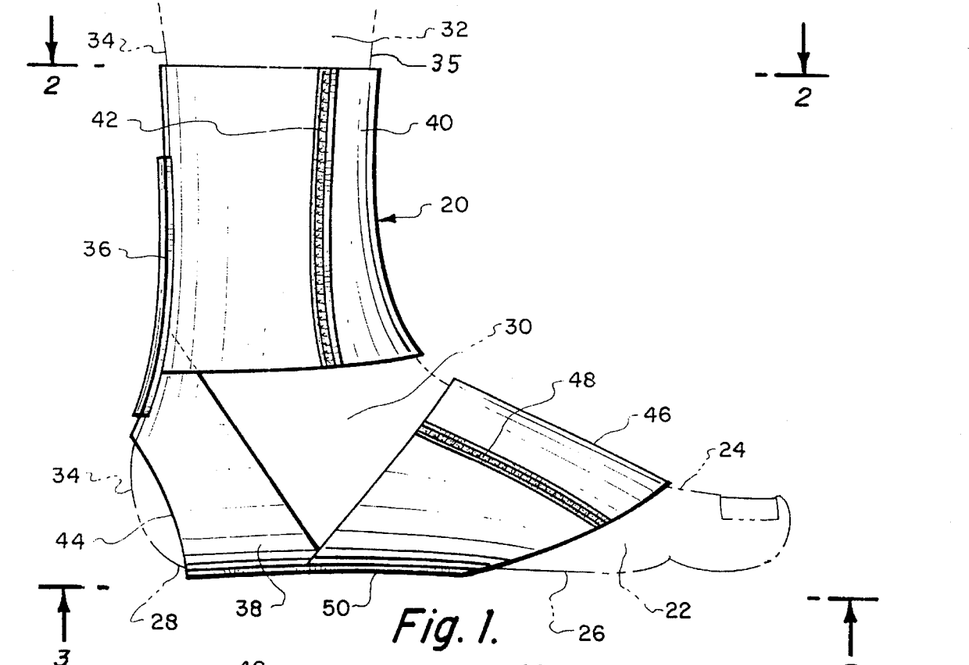
FIG. 1 is a side elevational view of a first embodiment of the jumping assist system of the present invention showing the jumping assist system being mounted in conjunction with the lower leg and foot of a human.
Figure 2:
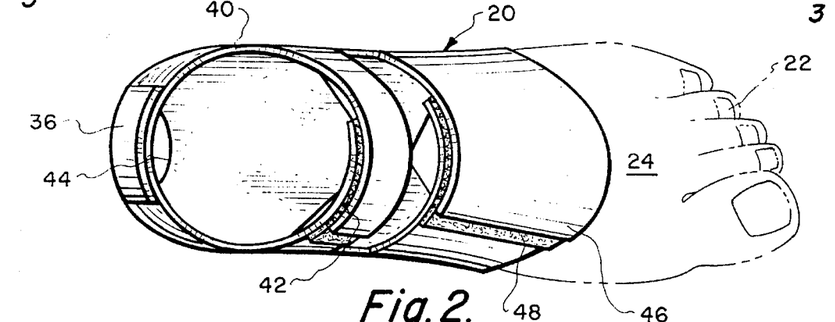
FIG. 2 is a top plan view of the system of FIG. 1 taken along line 2—2 of FIG. 1.
Figure 3:
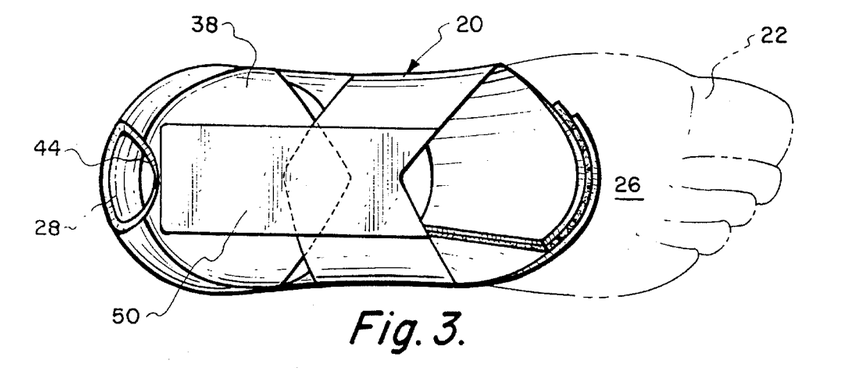
FIG. 3 is a bottom plan view of the first embodiment of the jumping assist system of the present invention taken along line 3—3 of FIG. 1.
Figure 4:
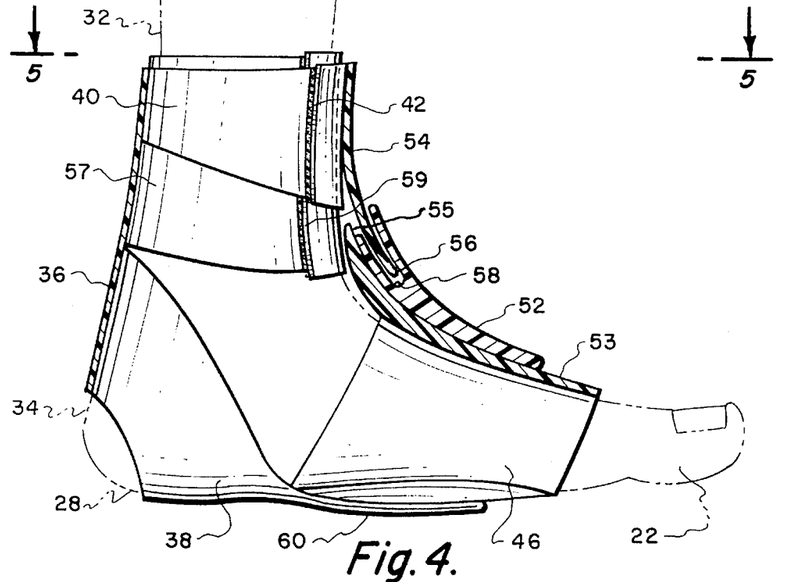
FIG. 4 is a modification of the jumping assist system of FIG. 1 showing the incorporation of a movement restricting brace device.
Figure 5:
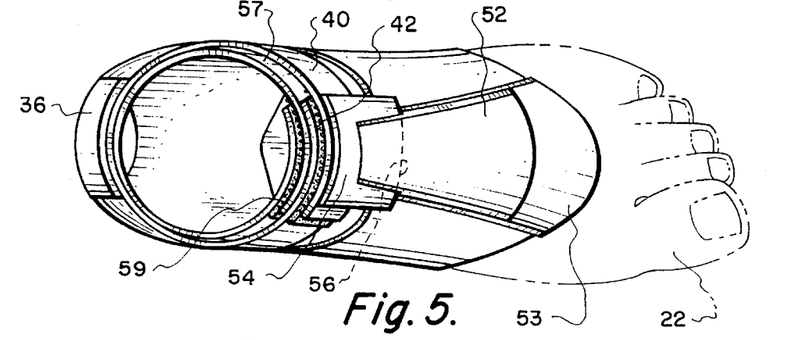
FIG. 5 is a top plan view showing more clearly the brace utilized in conjunction with FIG. 4 taken along line 5—5 of FIG. 4.

It has been found that when jumping, there is a tendency for the lower leg strap 40 to lower along the front of the leg 32. There is also a tendency for the dorsum tension brace 46 to rise toward the lower leg strap 40. Straps 40 and 46 must remain in a fixed position in order for maximum pulling force on the heel to be attained. Therefore, in order to prevent such movement from occurring, there may be incorporated on the exterior-most section of the dorsum tension brace 46 a movement restricting brace 52. This brace 52 will normally be constructed of a semi-rigid material such as plastic. Fixedly secured on the inside surface of the brace 52 is a padding layer 53. The padding layer 53 is fixedly mounted onto the dorsum tension brace 46. The padding layer 53 has an upward extension 55 which is to rest against a wrap-around padding 57 that is to be located against the leg of the user underneath lower leg strap 40. The free ends of the lower leg strap 40 are connected together by the releasable fastener 42. A similar fastener 59 connect together the ends of the padding layer 57.

Fixedly mounted on the exterior surface of the lower leg strap 40 is a position fixing brace 54. Position fixing brace 54 is constructed of the same material as movement restricting brace 52. The lower or leading edge 56 of the brace 54 rests within a channel or groove 58 formed within the brace 52. The upward extension of the padding 55 prevents the braces 52 and 54 from digging into the skin of the ankle as the user moves into the jump-ready position and brace 54 abuts brace 52.

It is also to be noticed that the heel sling 38 includes a forward extension 60 which rests within the arch area of the foot 22. The dorsum tension brace 46 is to be attached onto the forward extension 60. Normally, there will be located a padding type of material (not shown) in the area of the arch with this padding being fixed in position on the forward extension 60.

It is understood that position fixing braces 54 and 52 could be configured any number of ways, such as both partially encircling to the sides of the lower leg 32, or the brace 54 being as depicted but anchoring at the sides of the lower leg strap 40 to reduce pressure at the shin area. Braces 54 and 52 are to be free to move apart into the lift-off position with no resistance to each other, overlapping and abutting in such a way as to both impede the force of gravity pushing the leg forward at the optimum jump-ready position, thus increasing the transition speed from the jump-ready position to the lift off position, and maintain the position of the lower leg strap 40 and the dorsum tension brace 46 to provide maximum pulling force from the lower leg 32 to the heel 28. All padding could be accomplished by air filled bladders and augmented by air being forced from the bottom of the foot as the foot moves into the jump-ready position with the air being transferred to other areas requiring more protection. In fact, it is entirely possible that all the embodiments of this invention could be constructed of a plastic shoe more like the modern ski boot than the conventional basketball shoe, to provide easier means of attachment of braces to hold cables and straps in their proper positions, with all or most necessary padding accomplished by interlinking air chambers.

Figures 6, 6A:
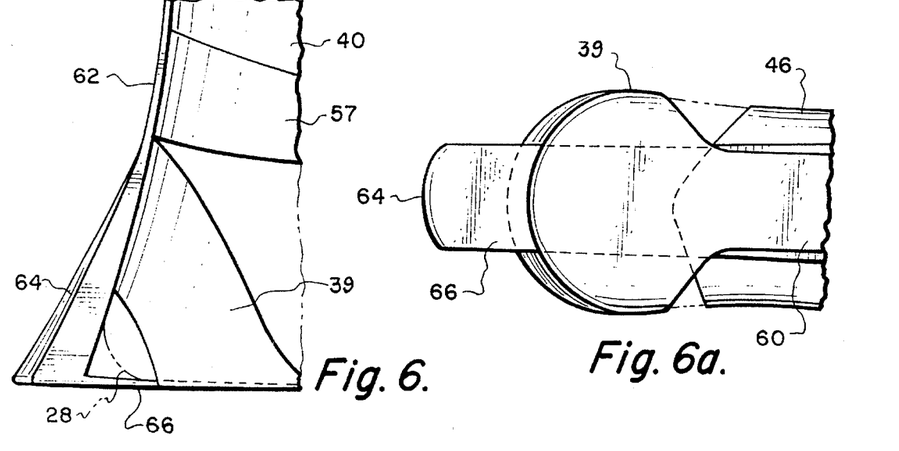
FIG. 6 is a segmental side elevational view of a modified form of the jumping assist system of this invention shown in FIGS. 1 to 5.
FIG. 6a is a segmental bottom plan view of the modified form of jumping assist system of FIG. 6.
Figure 7:
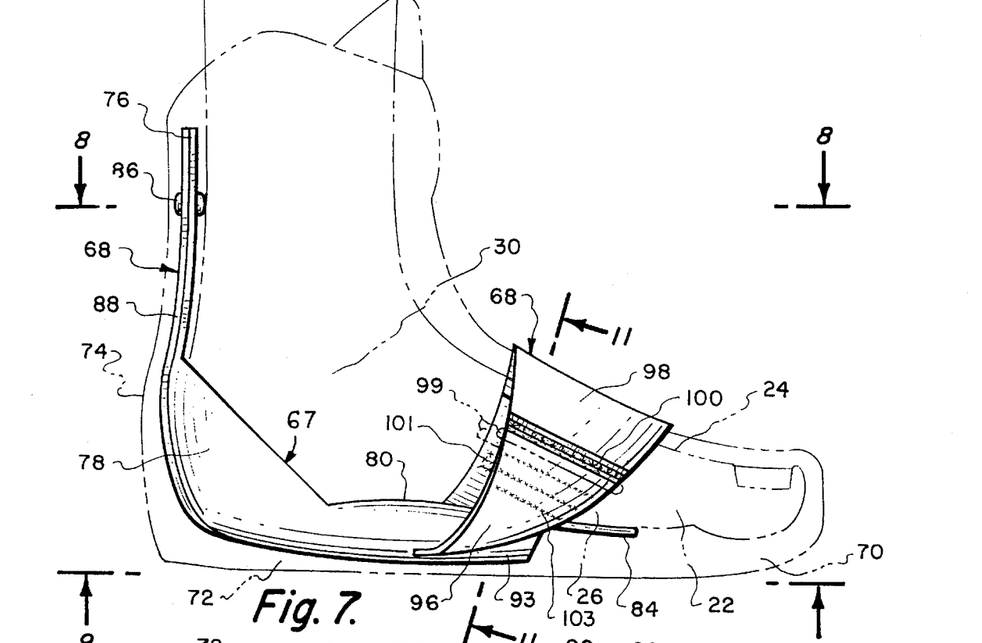
FIG. 7 is a side elevational view of a second embodiment of the jumping assist system of the present invention which is designed to be incorporated in conjunction with a shoe.
Figure 8:
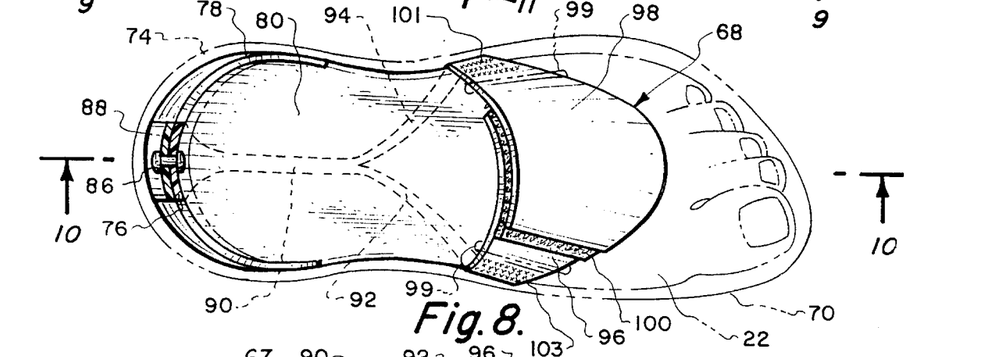
FIG. 8 is a top plan view of the jumping assist system of FIG. 7 taken along line 8—8 of FIG. 7.
Figure 9:
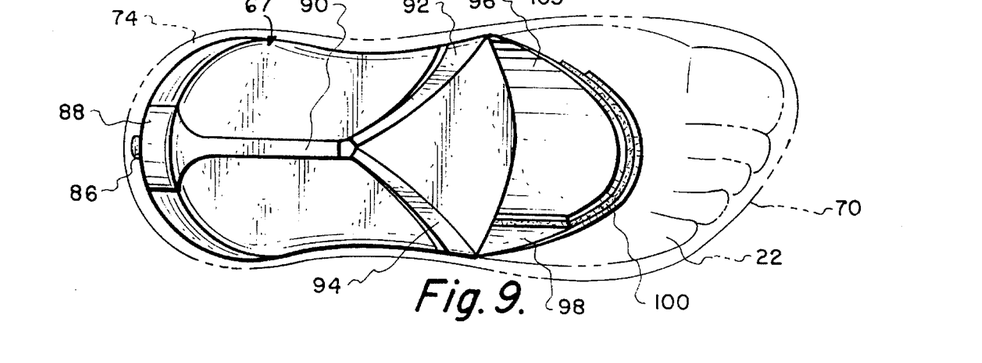
FIG. 9 is a bottom plan view of the jumping assist system of FIG. 7 taken along line 9—9 of FIG. 7.
Figure 10:
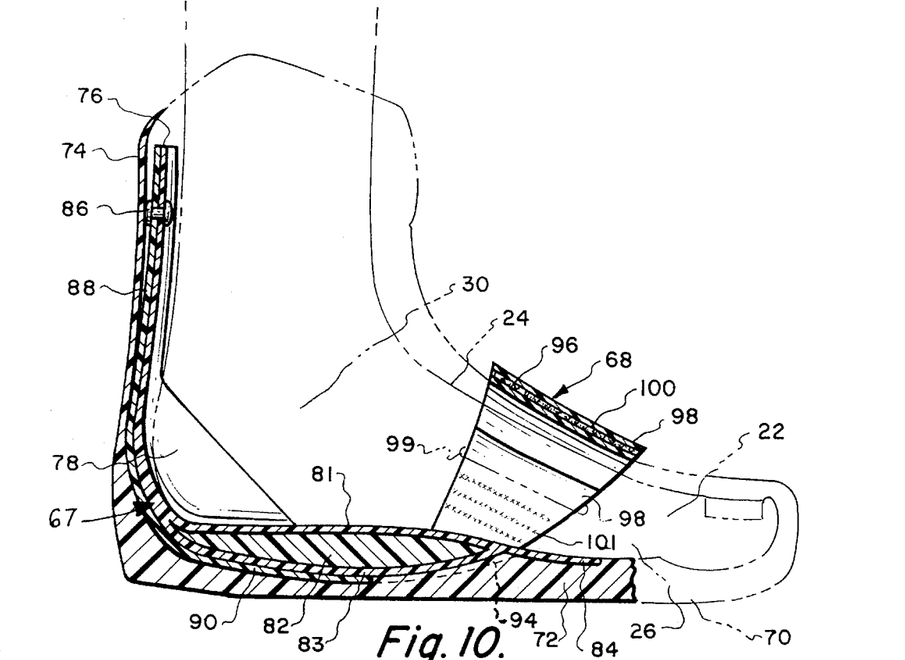
FIG. 10 is a longitudinal cross-sectional view through the jumping assist system of the second embodiment taken along line 10—10 of FIG. 8.
Figures 11, 12:
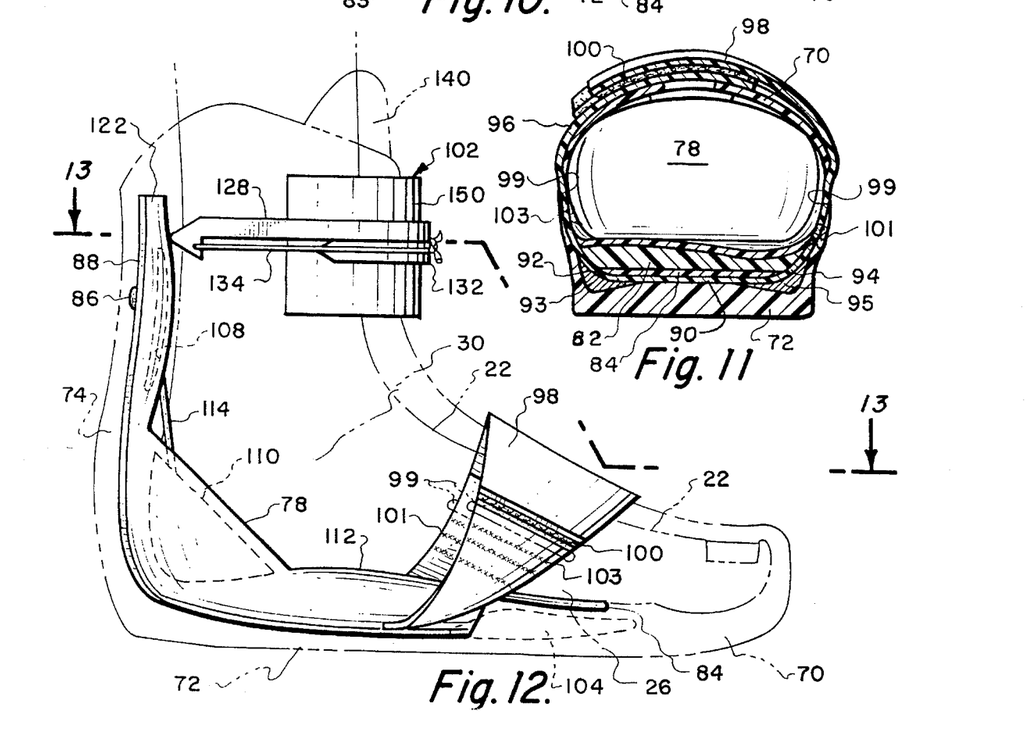
FIG. 11 is a transverse cross-sectional view through a portion of the jumping assist system of FIG. 7 taken along line 11—11 of FIG. 7.
FIG. 12 is a side elevational view of a further embodiment of the jumping assist system of this invention which is basically similar to that of FIG. 7 with the inclusion of additional structure to achieve increased energy level during leaping.
Figure 13:
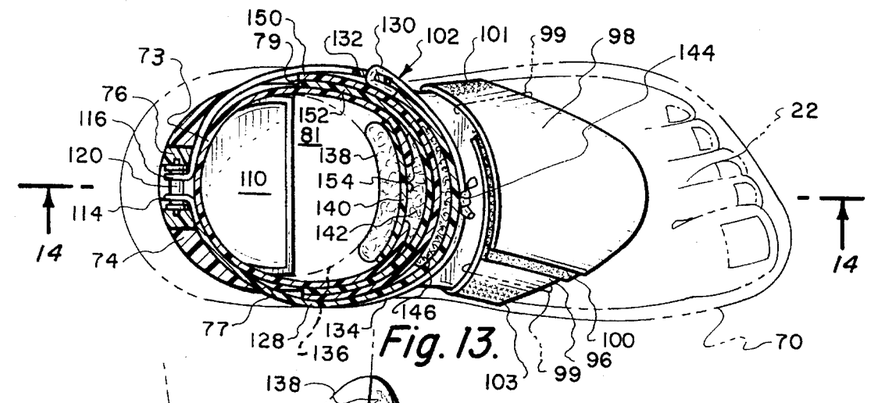
FIG. 13 is a top plan view of the jumping assist system of FIG. 12 taken along line 13—13 of FIG. 12.
Figure 14:
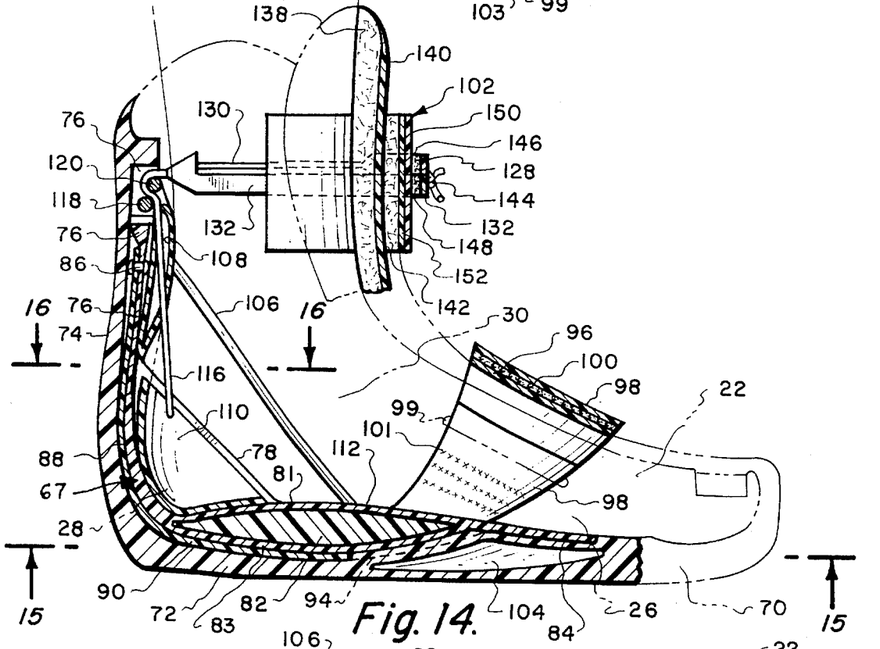
FIG. 14 is a longitudinal cross-sectional view of the jumping assist system of FIG. 13 taken along line 14—14 of FIG. 13.
Figure 15:
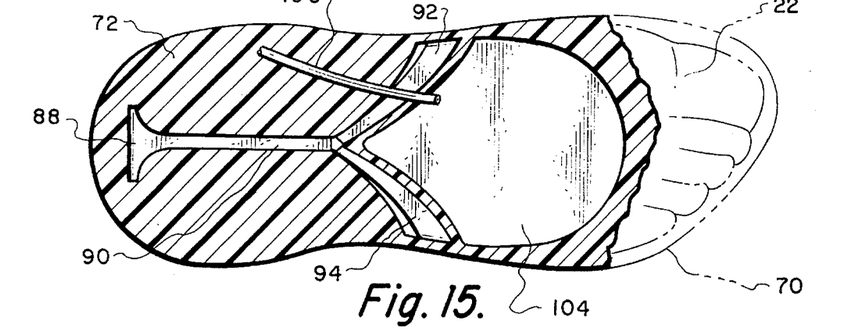
FIG. 15 is a longitudinal cross-sectional view along the bottom of the jumping assist system of FIG. 14 taken along line 15—15 of FIG. 14.
Figure 16:
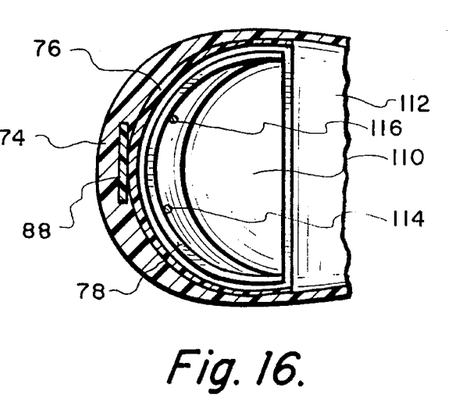
FIG. 16 is a transverse cross-sectional view through the jumping assist system of FIG. 14 taken along line 16—16 of FIG. 14.
Figure 17:
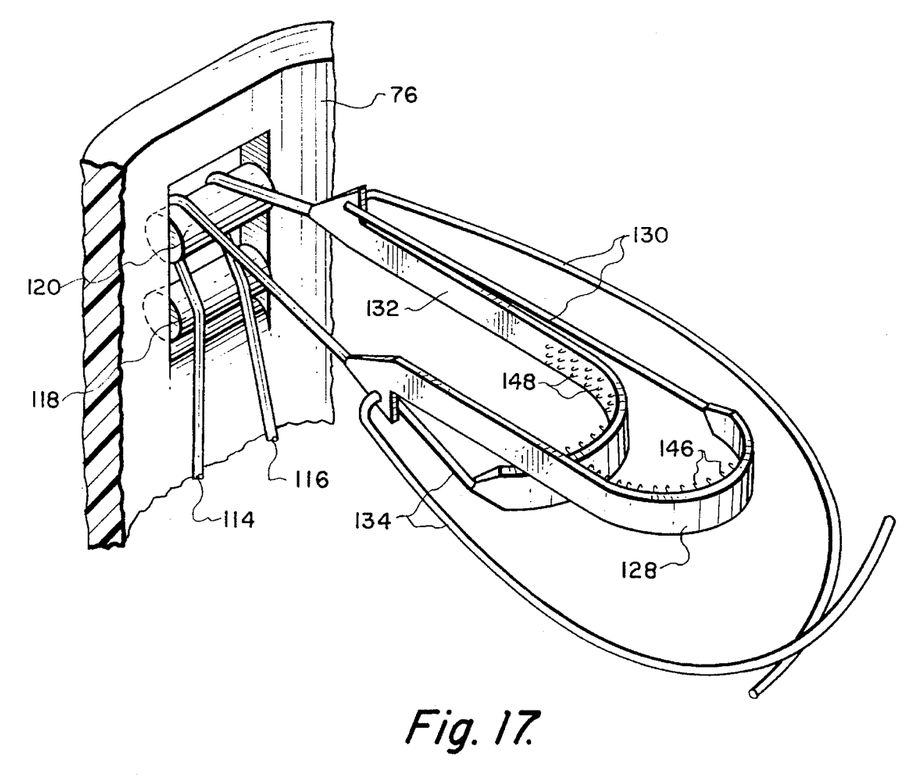
FIG. 17 is an exploded isometric view of a portion of the jumping assist system of FIGS. 12 to 16 showing more clearly the strap and cabling arrangement used in conjunction with this jumping assist system.

Referring particularly to FIGS. 6 and 6a, there is shown a modification of the jumping assist system 20 in which the tension brace 62 extends to the bottom a rigid heel cup 39 and includes a rearwardly extending tension brace 64. Connected to the brace 64 and in alignment with the bottom of the foot 22 is a rearward horizontal extension 66 which extends underneath the heel 28 and is integrally connected to the forward extension 60. Cup 39, forward extension 60 and rearward extension 66 would likely be constructed of spring steel or similar strong plastic. The extension 66 has been found to provide better leverage and smoother transition between leg movement forward and the resulting upward pull on the heel to the lift-off position. Also, the upward pulling force near the end of extension 66 creates a pivot axis under the heel 28 as the heel 28 becomes a fulcrum which causes a downward force at forward extension 60 helping to propel the foot into lift-off due to the desired rotation at ankle joint 30. Also, the extension 66 provides cushion to an individual's heel when walking, running or jumping. It should be noted that the rearward horizontal extension 66 could easily be incorporated into the further embodiments shown in FIGS. 7 to 17. Rearward horizontal extension 66 could also be angled toward the ground more than in the straight horizontal position shown in FIG. 6.

Referring particularly to FIGS. 7 to 11, there is shown a further embodiment 68 of the jumping assist system of this invention. Like numbers are utilized to refer to like parts when comparing FIGS. 7 to 11 with FIGS. 1 to 6. The jumping assist system 68 shown in FIGS. 7 to 11 is shown mounted within a shoe 70. The shoe 70 includes a cushiony sole 72 and an ankle support upper 74. Incorporated within the body of the shoe 70 is the jumping assist system 68 composed of a rigid angle brace 67 which supports a flexible dorsum tension brace composed of straps 88, 90, 92, 94, 96 and 98. The rigid, supporting angle brace 67 is composed of a vertical section 76 which is integrally connected to a heel cup 78, which is integrally connected with a horizontal section 80 composed of top wall 81 and bottom wall 83 which is located between the heel cup 78 and the ball 26 of the foot 22, which could be filled with various types of padding forming arch support 82. Forward of the arch support 82 and integrally connected with the horizontal section 80 is a ball support 84 of angle brace 67. Bottom wall 83 is strong, rigid and thickly contoured at edges 93 and 95 so as to maintain strips 92 and 94 (explanation to follow) in their correct positions. Top wall 81 could be equally strong and rigid at narrow portions along both its sides (not shown) but its middle section extending under the sensitive tendons under the arch would be more flexible or even open to the padding of arch support 82. Strap 88 is fixedly secured by rivet 86 to the vertical section 76. Strap 88 is to be constructed of a flexible material such as leather, canvas or other similar material which is basically inelastic. The vertical section 76 of angle brace 67 must be extremely strong, basically rigid, but could be like spring steel, and is further held in place by ankle support upper 74 of shoe 70. The strap 88 extends underneath the heel cup 78 and is integrally connected to strap position 90 and then is divided into a pair of strips 92 and 94 which angle upward to first strap 96 and second strap 98. Strip 92 is integrally or sewn to a first strap 96. Strip 94 is integral or sewn to the second strap 98. The straps 96 and 98 are to extend to the outer layer of shoe 70 through holes 99 and then overlap one another at the dorsum area 24 of the foot 22. The straps 96 and 98 are to be stitched at 101 and 103 and then further secured together by a releasable hook and eye fastening arrangement 100.

Straps 96 and 98 are to be tightly fixed over the portion of the shoe 70 located over the dorsum 24. Laces (not shown) of the shoe are to be tightly laced entirely up the ankle support upper 74. When the bottom surface of the foot contacts the floor momentarily under force of weight and motion, the result is a slight lengthening of the foot due to flattening of the arch. This causes a tightening of the strap 90, which is held in place by rivet 86 at ankle support upper 74, which produces an upward force at the arch and heel and also produces a slight pulling force downward at the dorsum magnified by the vertical slant of strips 92 and 94 due to contoured edges 93 and 95 which allows the user to make a quicker transition between the jump-ready position and the lift-off position.

More simply put, expansion of the foot begins as weight comes down on the ball going into the jump-ready, and continues until the heel touches the ground momentarily just before lift-off, causing stretching of the flexible dorsum tension brace from front dorsum to rear rivet 86. Since both points are above the heel and arch, a pull is generated on the heel/arch area if both anchor points hold.

It should be noted that the conventional arch support of the prior art is not of much value unless there is something supporting the arch support itself, which is the ground when standing flat footed. In jumping and running, however, the greatest gravity force that must be overcome occurs just after the heel leaves the ground, rendering conventional arch supports ineffective, even with an extremely rigid sole, because there is no pressure forcing the sole against the support during this stage of the jump. Part of the intention of the above described portion of the present invention, which we refer to more as the holding or supporting portion as opposed to the lifting portion (to be described further on) is to provide arch support during the time the user's weight is shifting to the ball of the foot.

To explain further how the arch support provided by the angle brace and dorsum tension brace improves jumping ability, the dorsum tension brace works in conjunction with those muscles in the sole of the foot (underlying the foot) which connect the heel to the ball, the action of these muscles being to hold or increase the curve of the transverse arch. These muscles hold the arch against spreading and collapsing under the individual's weight which allows the pulling force from the achilles area to carry through to the ball of the foot pulling the foot into an obtuse angle relative to the leg. The dorsum strap augments these muscles providing for less loss in energy during the transition between the jump-ready position and the lift-off position.

Now, referring particularly to FIGS. 12 to 17, there is the preferred embodiment 102 of the jumping assist system of this invention which incorporates the above described supporting angle brace and flexible dorsum tension brace with the previously described flexible achilles tension brace through the use of a cable and pulley type mechanism. As noted previously, a problem in attempting to provide pulling force from the shin to the heel is that the heel tends to gradually pull the strap at the shin downward toward the foot, so that the force of the strap from the shin pulling the heel up is eventually lost. The inventor believes this embodiment 102 will best overcome this problem. Again, like numerals have been utilized to refer to like parts. The jumping assist system 102 is incorporated within the shoe 70. The heel 28 is supported by a sling 110. The sling 110 normally rests against the inner sole 112 which lies within the rigid heel cup 78. One side edge of the sling 110 is connected to a cable 114 with the opposite side of the sling 110 being connected to a cable 116. Cables 114 and 116 extend between a pair of rollers 118 and 120 which are mounted near the top of the vertical section 76 of the angle brace 67.

Cable 114 is secured to one end of a leather strap 128 with the opposite end of the strap 128 being secured to a lace 130. Cable 116 is secured to one end of leather strap 132 with the opposite end of the strap 132 being fixedly secured to a lace 134. Against the shin 136 of the leg is a soft resilient tongue pad 138 and tongue leather 140 of the shoe 70. Pressing against the exterior surface of the tongue 140 is a shin pad 142. Mounted against the exterior surface of the shin pad 142 is a stiffener 152. On the exterior surface of stiffener 152 is a layer of VELCRO (tradename) loops 150. Abutting against loops 150 is VELCRO hook layers 146 and 148 mounted respectively on the inside surface of straps 128 and 132. These straps 128 and 132 are in vertical alignment and pressed against VELCRO loops 150 which are fixedly mounted on the stiffener 152. This stiffener 152 is essentially U-shaped with one leg of the U being attached to ankle support upper 174 at point 77 with the opposite leg of the stiffener 152 not being attached to the upper 74 but is free to move relative thereto and overlap leg cover 73 at point 79. This freedom of movement is necessary in order to permit entry and removal of the foot 22 within the shoe 70.

During entry and removal of the foot 22, upper 74 will open up or expand since upper 74 is open at the front forming tongue opening 154. In this embodiment, the regular shoe laces (not shown) would not extend to tongue opening area 154 but would end and tie just above dorsum strap 96. Once the foot 22 is installed within the shoe 70, the tongue opening 154 somewhat closed and the stiffener 152 overlays the tongue opening 154 thereby effectively closing such. Straps 128 and 132 are pulled snug and attached by VELCRO to stiffener 152. The laces 130 and 134 are to be further tightened by the human and then tied into a knot 144. This will cause the sling 110 to be snugly positioned under the heel 28.

When the human moves into the jump-ready position, a pulling action will occur on the cables 114 and 116 which will exert a pulling force on the heel 28 especially for the brief moment when the heel of the shoe in on the ground supporting extreme pressure at the pivot point of the cable at the roller 120 on the brace 67 which allows the user's heel to momentarily lift slightly above the inner sole of the shoe 70. Also, at this time, the foot 22 would tend to flatten and expand with a pulling and holding force being applied through the dorsum brace arrangement. Within the sole 72 is a bladder in the form of air chamber 104. A conduit 106 connects to chamber 104 with the opposite end of conduit 106 connecting with a similarly enclosed air bladder chamber 108. Air chamber 108 is located within upper section 74 of the shoe 70. When the individual leans forward and applies pressure to the ball 26 of the foot, the air confined within chamber 104 is pushed through conduit 106 into chamber 108. The air chamber 104 provides a cushioning for the ball 26 of the foot during the time that pressure is applied by the foot in the jump-ready position. More importantly, the air conducted within chamber 108 causes expansion thereof, which protects the achilles tendon and adds support to the achilles section 76 of the angle brace 67 against the force of the cables 114 and 116 pulled by the shin producing an increased value in the pulling force which will cause the human to jump to a greater height.

To clarify the jumping assist system of this invention, as the jumper initially contacts the ground with the balls of his or her feet and legs are only slightly bent, the dorsum tension brace at strap 90 exerts upward pressure (a holding force) on arch support 82 as the jumper's weight on ball 26 causes expansion of foot 22 and the tightening of the dorsum tension brace. It is after this initial contact with the ground that the achilles tension brace goes into effect which is when the legs of the jumper bend further and the heel of the shoe 70 supporting angle brace 67 contacts the ground just before lift-off.

What is claimed is:

1. In combination with an ankle and a foot attached to a lower leg of a human at an ankle joint, said lower leg having a front surface defined as a shin, said lower leg also having a back which includes an achilles tendon, an achilles area located directly adjacent said achilles tendon, said foot having a bottom surface with a ball and toes located at the front and a heel located at the rear, said foot having a curved transverse arch which has arch muscles connecting said heel and said toes, said arch muscles function to increase the curve of said transverse arch, the upper surface of said foot located directly adjacent said toes being defined as the dorsum, said foot being movable at said ankle joint to form an acute angle in a jump-ready position and then form an obtuse angle in a lift-off position during jumping off the ground, with said foot in said jump-ready position said shin moves forwardly toward said foot which lengthens said achilles tendon, the height of said jumping is increased the faster said achilles tendon contracts pulling up at said heel which rotates said foot at said ankle joint with said front of said foot moving into said lift-off position, said foot being located in a shoe, a jumping assist system mounted in conjunction with said shoe, said shoe having a sole and an ankle support upper, said jumping assist system comprising:

a flexible achilles tension brace extending between said lower leg and the portion of said bottom surface located directly adjacent said heel, a heel sling surrounding said heel, said achilles tension brace being anchored at said shin and extending to said achilles area and then extending to said heel sling, an angle brace extending from said achilles area to said sole of said shoe and extending underneath said heel sling to said ball of said foot, a pulley located at said achilles area and attached to said angle brace, said pulley being spaced from said lower leg and fixed in position relative to said lower leg, said achilles tension brace being freely movable relative to said pulley, whereby as said lower leg moves into said jump-ready position a force is exerted on said lower leg and said heel such that the opposing force of said lower leg from the forward weight and motion of the body of the human will assist in overcoming resistance at said heel due to gravity thus applying a pulling force pulling said heel upward increasing the propulsion of the jump.

2. The combination as defined in claim 1 wherein:

a dorsum tension brace interconnecting said dorsum and said angle brace, said dorsum tension brace is anchored directly adjacent said pulley and extends below said heel sling and said angle brace to said ball and then branching into straps encircling said front of said foot in the area of said dorsum, said dorsum tension brace receiving tension from the expansion force due to the spreading of said foot when said ball contacts the ground under the weight of said human, said tension exerting a force upward on said transverse arch and said heel of said foot and downward at said dorsum, said force aiding said arch muscles in maintaining the shape of said transverse arch enabling more energy to flow from said lower leg to said ball at said lift-off position, said dorsum tension brace also serving to hold said angle brace in a correct position increasing the pulling tension of said achilles tension brace between said lower leg and said heel.

3. The combination as defined in claim 1 wherein:

said angle brace being anchored within said sole and being approximately the same in width as said sole.

4. The combination as defined in claim 1 wherein:

said angle brace has an arch support which connects with said transverse arch.

5. The combination as defined in claim 4 wherein:

said arch support having an upper wall which is concave to said bottom surface of said foot and a lower wall which is convex to said bottom surface.

6. The combination as defined in claim 5 wherein:

said dorsum tension brace causing increased pressure under said transverse arch in said jump-ready position.

7. The combination as defined in claim 6 wherein:

a bladder forming a first air chamber located between said angle brace and said achilles tendon to cushion said achilles tendon and provide support for said angle brace.

8. The combination as defined in claim 7 wherein:

a second air chamber located against said bottom surface of said foot, an air passage tube interconnecting said first air chamber and said second air chamber, said air passage tube functioning to cause air to be conducted from said second air chamber into said first air chamber as said foot moves into said jump-ready position.

9. In combination with a foot having a bottom surface with a heel located rearwardly and a top surface with a dorsum located forwardly, forwardly of said heel is a ball with an arch interconnecting said heel and said ball, a lower leg including an achilles tendon extending vertically from said heel, said lower leg including a shin, said achilles tendon located at the rear of said leg with said shin located at the front of said leg, a shoe having a sole and an outer covering, an angle brace anchored in said sole of said shoe having a horizontal section extending from under said ball of said foot rearwardly towards said heel, said horizontal section contouring said arch and encasing said heel referred to as a heel cup, a vertical section extending vertically adjacent said achilles tendon forming with said horizontal section a right angle support brace, when said lower leg moves forwardly into a jump-ready position the distance between said lower leg and said vertical section increases, said angle brace serving to support and guide a dorsum tension brace which is flexible but non-elastic, said dorsum tension brace being anchored at said vertical section of said angle brace contouring said heel cup and extending under said horizontal section in said sole of said shoe to said ball, said dorsum tension brace at said ball branching into two straps surrounding said outer covering of said shoe, said straps being anchored at said dorsum.

10. The combination as defined in claim 9 wherein:

said horizontal section of said angle brace having a contoured edge establishing a pivot point under said bottom surface for said dorsum tension brace, when said foot widens and lengthens due to flattening from downward force a tension is created on said dorsum tension brace which applies to force against said bottom surface of said foot.

11. The combination as defined in claim 9 wherein:

said angle brace serving to guide an achilles tension brace between said lower leg and said heel in juxtaposition with said achilles tendon, said achilles tension brace being connected to said lower leg at an anchoring point.

12. The combination as defined in claim 11 wherein:

said vertical portion of said angle brace having a pulley mechanism which guides said achilles tension brace parallel to said bottom surface from said anchoring point and then vertically to said heel so that forward motion of said lower leg creates a force directly under said heel.

13. The combination as defined in claim 12 wherein:

said achilles tension brace extends from a sling mounted under said heel, said achilles tension brace having a pair of sides located opposite each other and including at least one cable on each said side to reduce friction at said pulley mechanism, said cable being integrally connected to a fastener arrangement which anchors at said shin and further including laces which extend completely around said lower leg to tie against said fastener arrangement, said fastener arrangement to resist the force against said shin by said heel as said lower leg moves into said jump-ready position.

14. In combination with an ankle and a foot attached to the lower leg of a human at an ankle joint, said lower leg having a front section defined as a shin and rear section which includes an achilles tendon, an achilles area located directly adjacent said achilles tendon, said foot having a bottom surface with a ball located forwardly and a heel located rearwardly with an arch located therebetween, the forward top portion of said foot being defined as the dorsum, said foot being movable at said ankle joint upward forming an acute angle with said lower leg in a jump-ready position where said foot still rests against a supporting surface, said foot to be movable downward forming an obtuse angle with said lower leg in a lift-off position when said heel is spaced from the supporting surface, with said foot in said jump-ready position said shin moves forwardly toward said foot which lengthens said achilles tendon, jumping height is increased the faster said achilles tendon contracts which moves said foot downward into said lift-off position, a jumping assist system for the human comprising:

an achilles tension brace consisting of a flexible member extending in a direction parallel to said bottom surface from said shin to said achilles area and also having a portion extending in a direction approximately perpendicular to said bottom surface to a heel sling which surrounds said bottom surface in the area of said heel, a pulling force being applied by said achilles tension brace upward on said heel when said shin moves forward in said jump-ready position tending to move said foot from said jump-ready position to said lift-off position which assists the human in jumping to a greater height when compared to the height obtained by the human without using said jumping assist system.

15. In combination with an ankle and a foot attached to the lower leg of a human at an ankle joint, said lower leg having a front section defined as a shin and rear section which includes an achilles tendon, an achilles area located directly adjacent said achilles tendon, said foot having a bottom surface with a ball located forwardly and a heel located rearwardly with an arch located therebetween, the forward top portion of said foot being defined as the dorsum, said foot being movable at said ankle joint upward forming an acute angle with said lower leg in a jump-ready position where said foot still rests against a supporting surface, said foot to be movable downward forming an obtuse angle with said lower leg in a lift-off position when said heel is spaced from the supporting surface, with said foot in said jump-ready position said shin moves forwardly toward said foot which lengthens said achilles tendon, jumping height is increased the faster said achilles tendon contracts which moves said foot downward into said lift-off position, a jumping assist system for the human comprising:

an achilles tension brace consisting of a flexible member extending in a direction parallel to said bottom surface from said shin to said achilles area and also having a portion extending in a direction approximately perpendicular to said bottom surface to a heel sling which surrounds said bottom surface in the area of said heel, a pulling force being applied by said achilles tension brace upward on said heel when said shin moves forward in said jump-ready position tending to move said foot from said jump-ready position to said lift-off position which assists the human jumping to a greater height when compared to the height obtained by the human without using said jumping assist system; and a dorsum strap encasing said dorsum, said dorsum strap being integrally connected to a flexible dorsum tension brace, said flexible dorsum tension brace extending under said bottom surface from said ball to said heel and upwards to connect at said achilles area such that any expansion pressure on said foot or forward movement at said achilles area will create added tension thus exerting a force downward at said dorsum and upwards at said heel and said arch.

16. The combination as defined in claim 15 wherein:

said jumping assist system being mounted in conjunction with a shoe.

17. The combination as defined in claim 16 wherein:

said jumping system being integrally mounted within said shoe.

18. The combination as defined in claim 17 wherein:

a bladder forming a first air chamber located between said tension brace and said achilles area to cushion said achilles tendon.

19. The combination as defined in claim 18 wherein:

a second air chamber located against said bottom surface of said foot, an air passage tube interconnecting said first air chamber and said second air chamber, said air passage tube functioning to cause air to be conducted from said second air chamber into said first air chamber as said foot moves into said jump-ready position.

20. In combination with an ankle and a foot attached to the lower leg of a human at the ankle joint, said lower leg having a front section defined as a shin and rear section defined as an achilles area, said foot having a bottom surface with a ball located forwardly and a heel located rearwardly with an arch located therebetween, the forward top portion of said foot being defined as the dorsum, said foot being movable at said ankle joint upward forming an acute angle with said lower leg in the jump-ready position and then downward forming an obtuse angle with said lower leg in the lift-off position, with said foot in said jump-ready position said shin moves forwardly toward said foot which lengthens the achilles tendon which is located in said achilles area, the jumping height is increased the faster the achilles tendon contracts which moves said foot downward into said lift-off position, a jumping system for the human comprising:

a leg strap extending between said shin and said achilles area, a tension brace located at said achilles area and extending to said bottom surface at said heel, said leg strap being fixed to said achilles tension brace, a pulling force being applied by said achilles tension brace upward on said heel when said shin moves forward in said jump-ready position tending to move said foot from said jump-ready position to said lift-off position which assists the human in jumping to a greater height when compared to the height obtained by the human without using said jumping system;

a heel sling surrounding said heel, said achilles tension brace being fixedly secured to said heel sling; and a dorsum strap encasing said dorsum, said dorsum strap being integrally connected to a flexible dorsum tension brace, said flexible dorsum tension brace extending under said bottom surface from said ball to said heel and upwards to connect at said achilles area such that any expansion pressure on said foot or forward movement at said achilles area will create added tension thus exerting a force downward at said dorsum and upwards at said heel and said arch.

21. The combination as defined in claim 20 wherein:

means for restricting the movement of said leg strap toward said dorsum strap when said foot moves into said jump-ready position.

22. The combination as defined in claim 21 wherein:

a portion of said heel sling comprises a forward extension which extends from said heel to contour the arch and terminate at said ball of said foot.

23. The combination as defined in claim 22 wherein:

said dorsum strap being secured to said forward extension.

24. The combination as defined in claim 20 wherein:

said dorsum strap extends under said bottom surface to connect at said achilles area.

25. The combination as defined in claim 24 wherein:

said jumping system being mounted in conjunction with a shoe.

26. The combination as defined in claim 25 wherein:

said jumping system being integrally mounted within said shoe.

27. The combination as defined in claim 26 wherein:

a bladder forming a first air chamber located between said tension brace and said achilles area to cushion the achilles tendon.

28. The combination as defined in claim 27 wherein:

a second air chamber located against said bottom surface of said foot, and air passage tubes interconnecting said first air chamber and said second air chamber, said air passage tubes functioning to cause air to be conducted from said second air chamber into said first air chamber as said foot moves into said jump-ready position.

* * * * *